United States Patent
McMinn

(10) Patent No.: US 7,878,989 B2
(45) Date of Patent: Feb. 1, 2011

(54) KNEE PROSTHESES

(76) Inventor: Derek James Wallace McMinn, Calcot Farm, Calcot Hill, Clent, Sourbridge, West Midlands (GB) DY9 9RX ( * ) Notice: Subject to any disclaimer, the term of this patent is extended or adjusted under 35 U.S.C. 154(b) by 1026 days.

(21) Appl. No.: 11/616,399

(22) Filed: Dec. 27, 2006

(65) Prior Publication Data

US 2007/0150066 A1 Jun. 28, 2007

(30) Foreign Application Priority Data

Dec. 28, 2005 (GB) ................................ 0526385.0

(51) Int. Cl.
| | |
|---|---|
| A61B 5/06 | (2006.01) |
| A61B 5/103 | (2006.01) |
| A61B 5/117 | (2006.01) |
| A61B 17/58 | (2006.01) |
| A61B 17/60 | (2006.01) |
| A61F 5/00 | (2006.01) |
| A61F 2/00 | (2006.01) |
| A61F 2/28 | (2006.01) |
| A61F 2/30 | (2006.01) |
| A61F 2/38 | (2006.01) |

(52) U.S. Cl. ................. 600/587; 600/550; 600/595; 606/87; 606/88; 606/89; 623/16.11; 623/18.11; 623/20.14; 623/20.2; 623/20.19

(58) Field of Classification Search ............ 600/550, 600/587, 595; 606/87–89; 623/16.11, 18.11, 623/20.14, 20.18, 20.19, 20.2

See application file for complete search history.

(56) References Cited

U.S. PATENT DOCUMENTS

| 4,158,894 A | 6/1979 | Worrell |
| 4,309,778 A | 1/1982 | Buechel et al. |
| 4,353,135 A | 10/1982 | Forte et al. |
| 4,583,555 A * | 4/1986 | Malcom et al. ............. 600/595 |
| 5,507,820 A * | 4/1996 | Pappas ..................... 623/20.19 |
| 5,597,379 A * | 1/1997 | Haines et al. ................. 606/80 |

(Continued)

FOREIGN PATENT DOCUMENTS

EP 0626156 A2 11/1994

(Continued)

OTHER PUBLICATIONS

Chun-Hsiung Huang, MD, et al., "Polyethylene Failure of the Patellar Component in New Jersey Low-Contact Stress Total Knee Arthroplasties", The Journal of Arthroplasty, 2005, vol. 20, No. 2, pp. 202-208.

(Continued)

Primary Examiner—Max Hindenburg
Assistant Examiner—Sean P Dougherty
(74) Attorney, Agent, or Firm—Foley & Lardner LLP

(57) ABSTRACT

A total knee prosthesis comprises a femoral component and a patellar component. The femoral component has a patellar flange into which is built a twist or roller coaster configuration. The patellar component has an off-set dome with respective lateral and medial facets. The configuration of the patellar flange resists forces from a medial to a lateral direction, whilst the lateral and medial facets of the patellar component are respectively shaped to allow area contact and line contact respectively with the femoral component. Also disclosed is a device for intra-operative checking of patellar tracking to allow correct insertion of the femoral and patellar components.

14 Claims, 18 Drawing Sheets

U.S. PATENT DOCUMENTS

| | | | | |
|---|---|---|---|---|
| 5,683,468 | A * | 11/1997 | Pappas | 623/20.29 |
| 5,713,897 | A * | 2/1998 | Goble et al. | 606/53 |
| 5,723,016 | A * | 3/1998 | Minns et al. | 623/20.2 |
| 5,871,540 | A | 2/1999 | Weissman et al. | |
| 5,879,392 | A * | 3/1999 | McMinn | 623/20.28 |
| 6,004,351 | A * | 12/1999 | Tomita et al. | 623/2.21 |
| 6,056,756 | A * | 5/2000 | Eng et al. | 606/87 |
| 6,846,329 | B2 * | 1/2005 | McMinn | 623/20.14 |
| 7,156,853 | B2 * | 1/2007 | Muratsu | 606/102 |
| 2003/0120346 | A1 | 6/2003 | Mercinek et al. | |
| 2003/0163201 | A1 * | 8/2003 | McMinn | 623/20.29 |
| 2004/0122441 | A1 * | 6/2004 | Muratsu | 606/102 |
| 2006/0052795 | A1 * | 3/2006 | White | 606/102 |
| 2006/0265078 | A1 * | 11/2006 | McMinn | 623/20.14 |
| 2007/0173946 | A1 * | 7/2007 | Bonutti | 623/20.14 |
| 2007/0219639 | A1 * | 9/2007 | Otto et al. | 623/20.19 |
| 2007/0293868 | A1 * | 12/2007 | Delfosse et al. | 606/88 |
| 2008/0091209 | A1 * | 4/2008 | Schmotzer et al. | 606/88 |

FOREIGN PATENT DOCUMENTS

| | | |
|---|---|---|
| EP | 0678011AO | 10/1995 |
| EP | 0773756 B1 | 10/2002 |
| EP | 1582184 A1 * | 10/2005 |
| EP | 1591083 A1 | 11/2005 |
| FR | 2594323 A1 | 8/1987 |
| FR | 2737848 A1 | 2/1997 |
| GB | 2253147 A | 9/1992 |
| GB | 2387546 A | 10/2003 |
| GB | 2426200 A | 11/2006 |
| WO | WO 93/00871 A1 | 1/1993 |
| WO | WO2005046532 A2 | 5/2005 |

OTHER PUBLICATIONS

Search Report dated Mar. 6, 2008 from related Great Britain application No. 0625584.8.

* cited by examiner

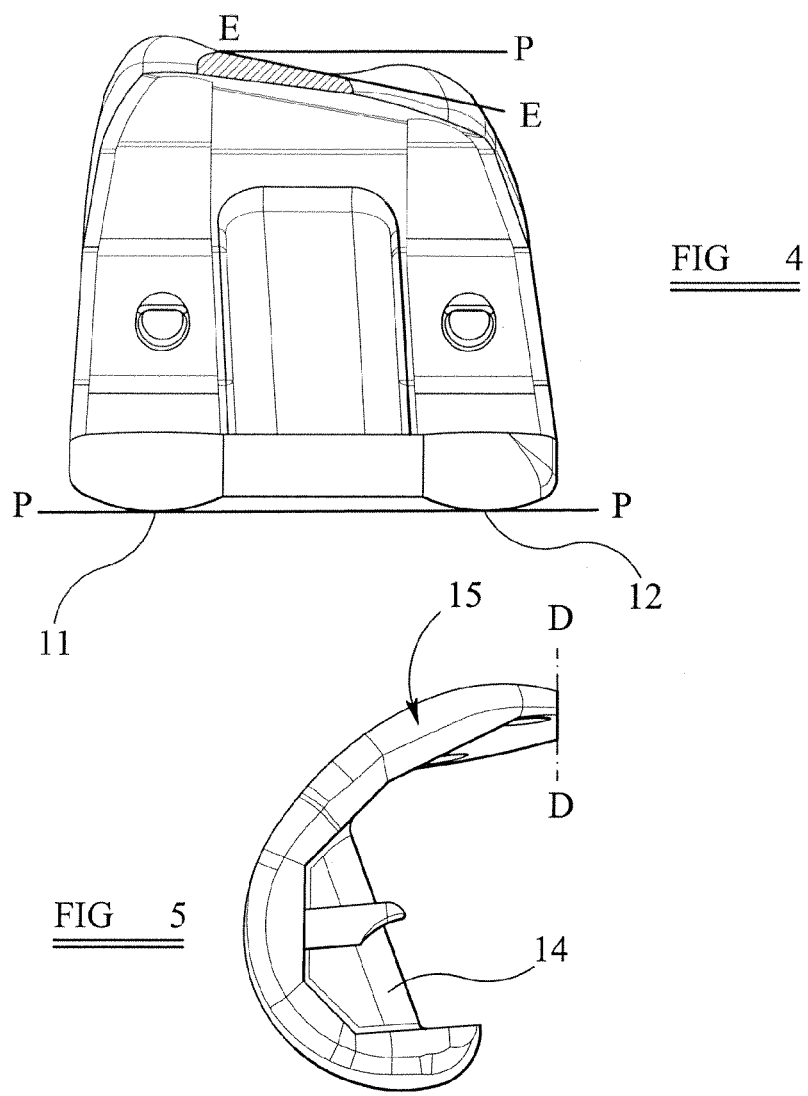
FIG 4
FIG 5
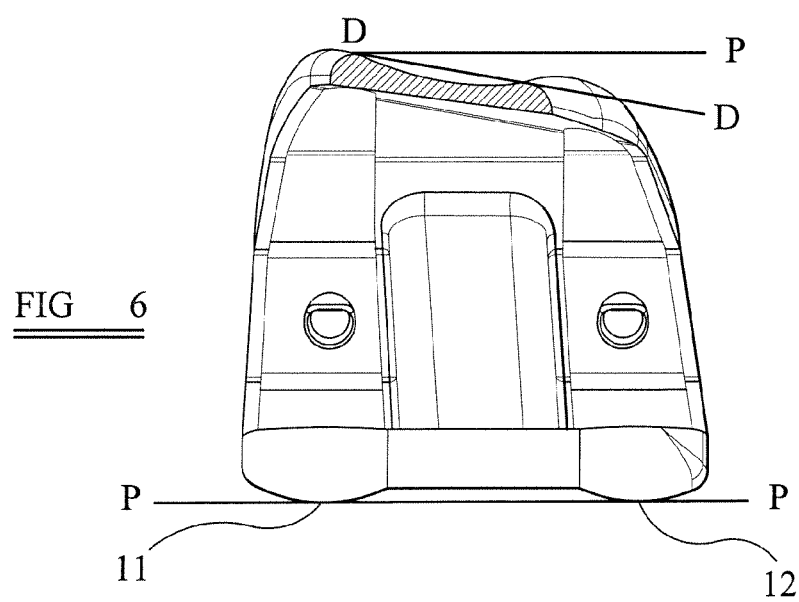
FIG 6

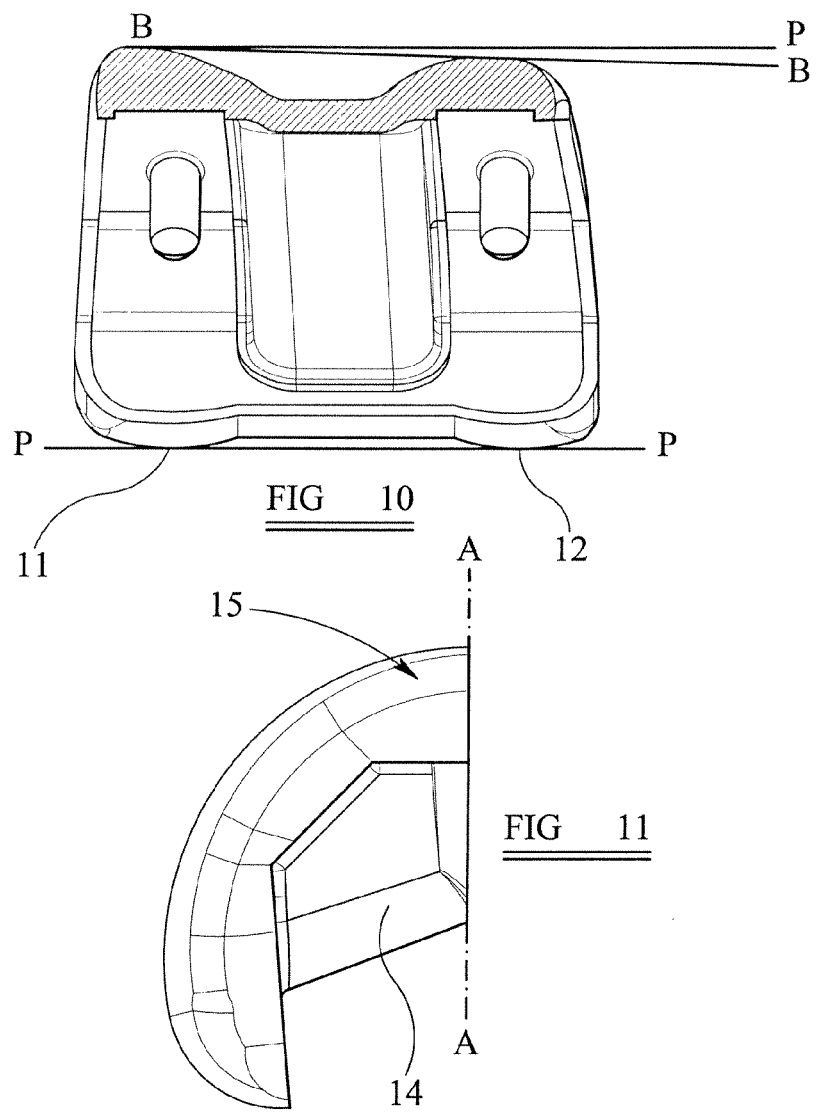
FIG 10
FIG 11
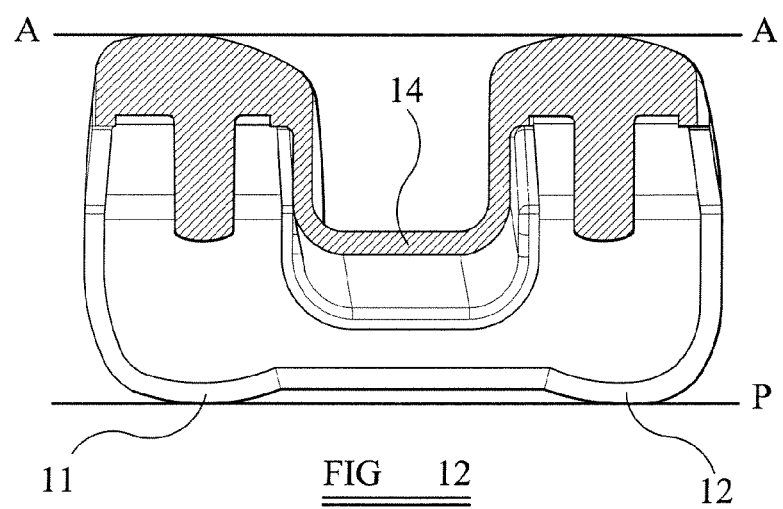
FIG 12

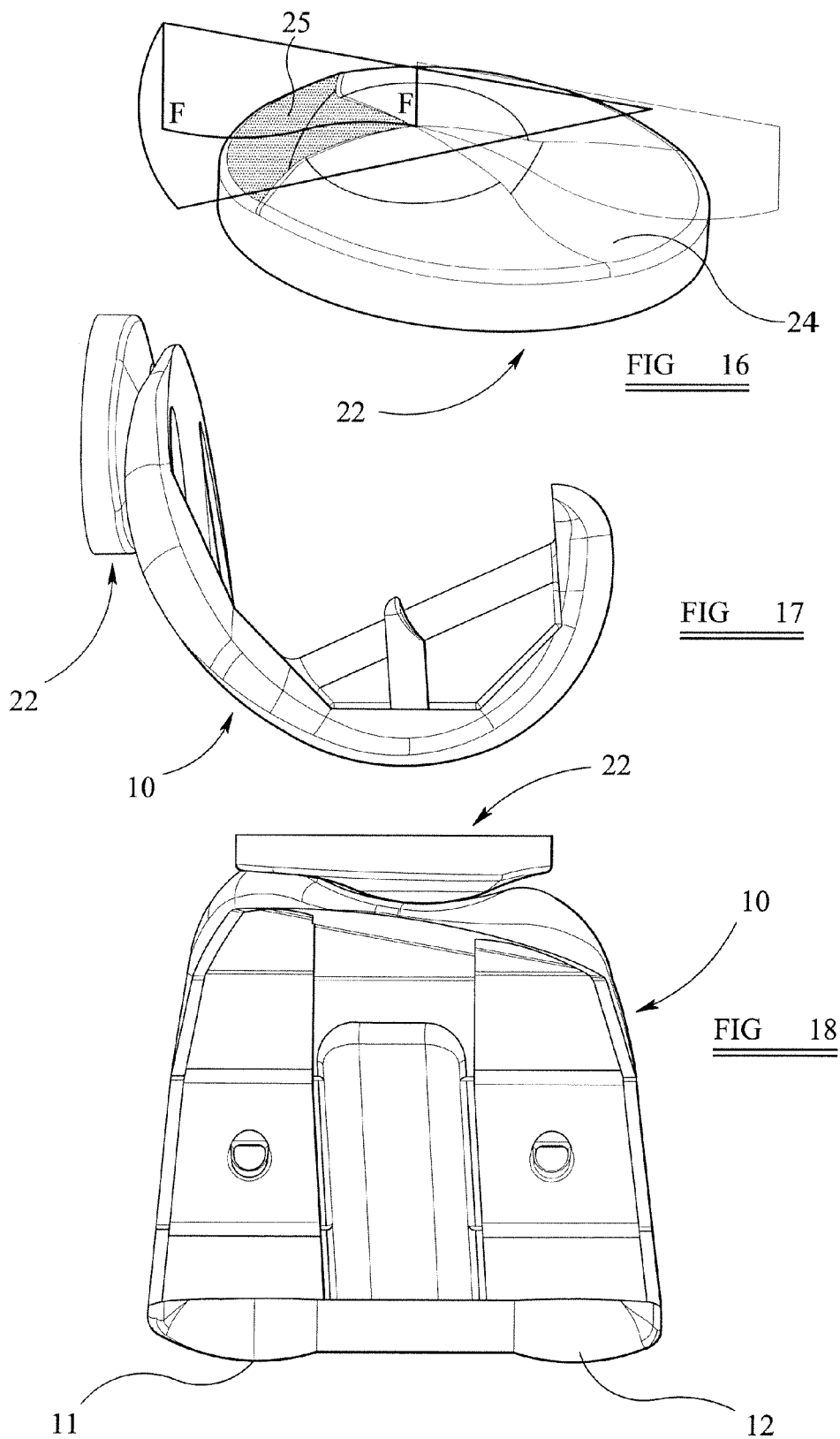

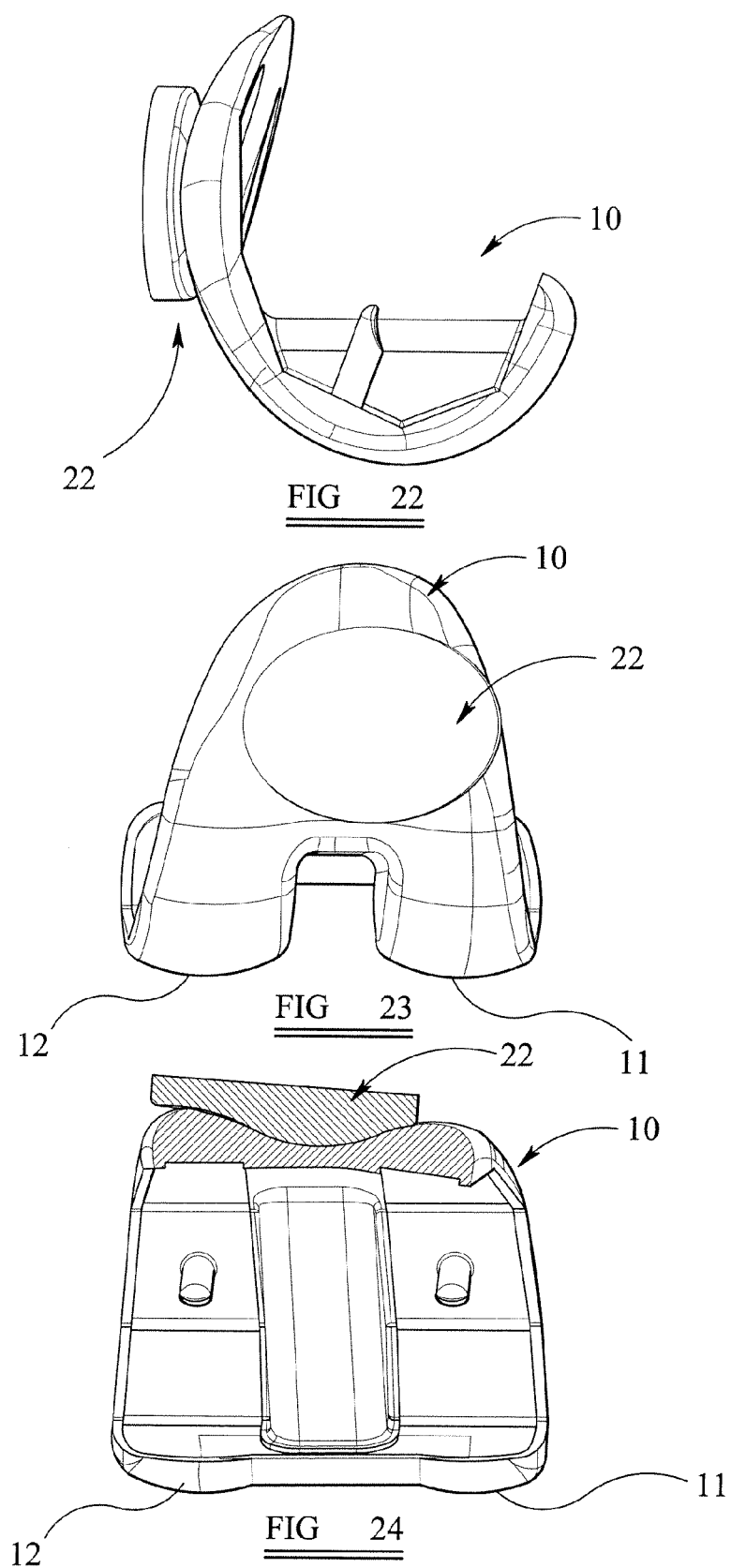

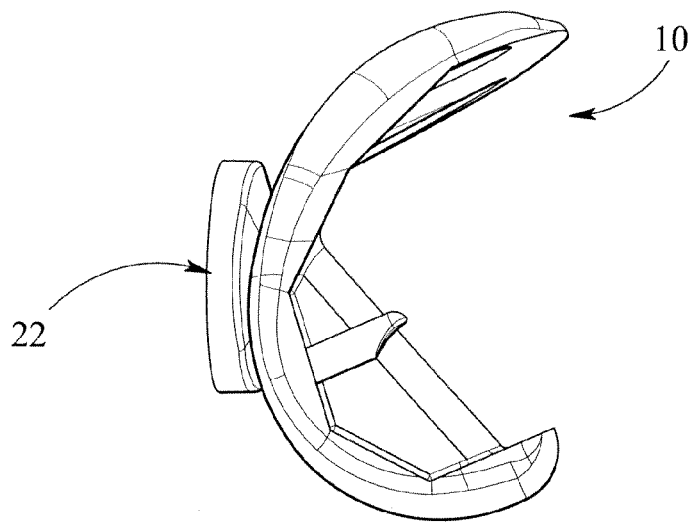
FIG 25
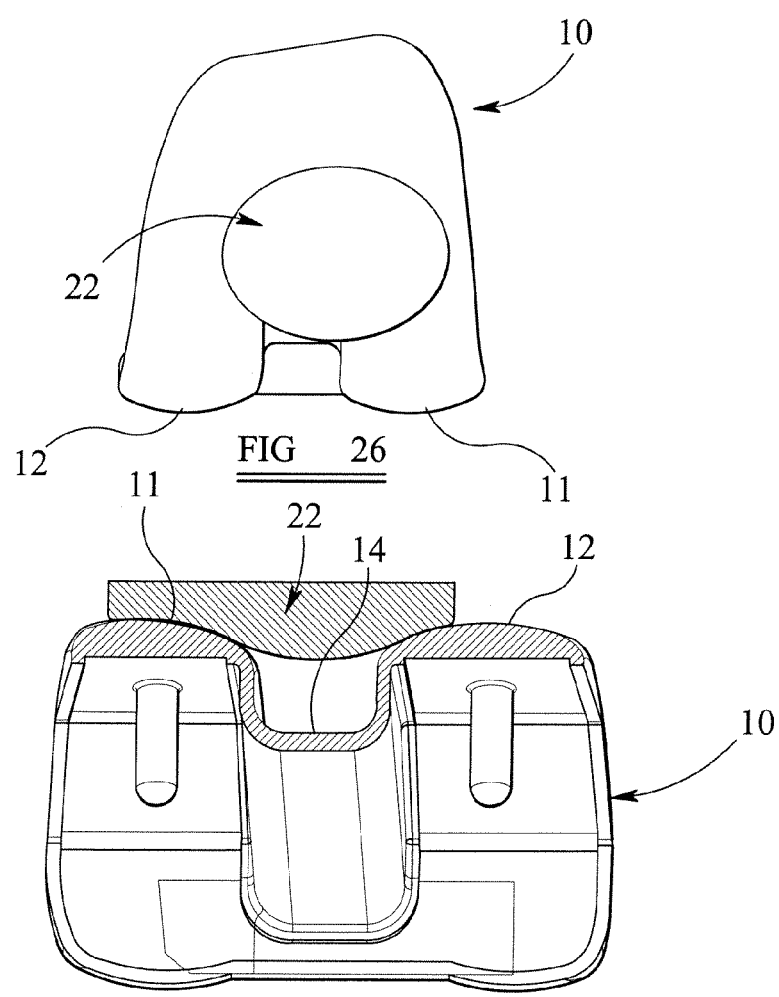
FIG 26
FIG 27

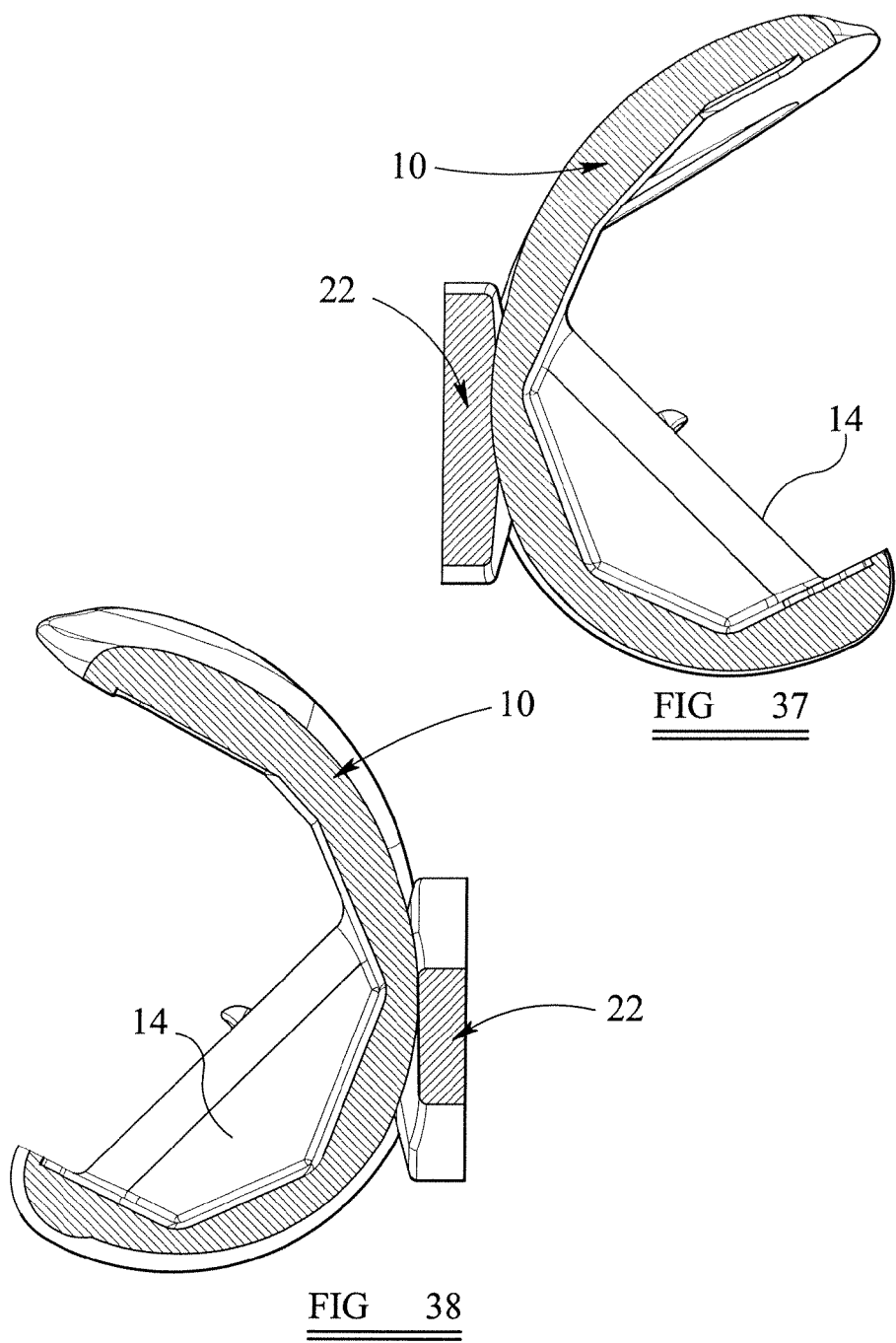
FIG 37
FIG 38
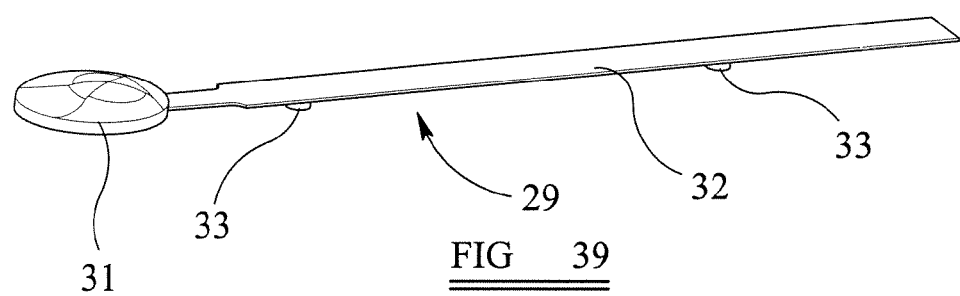
FIG 39

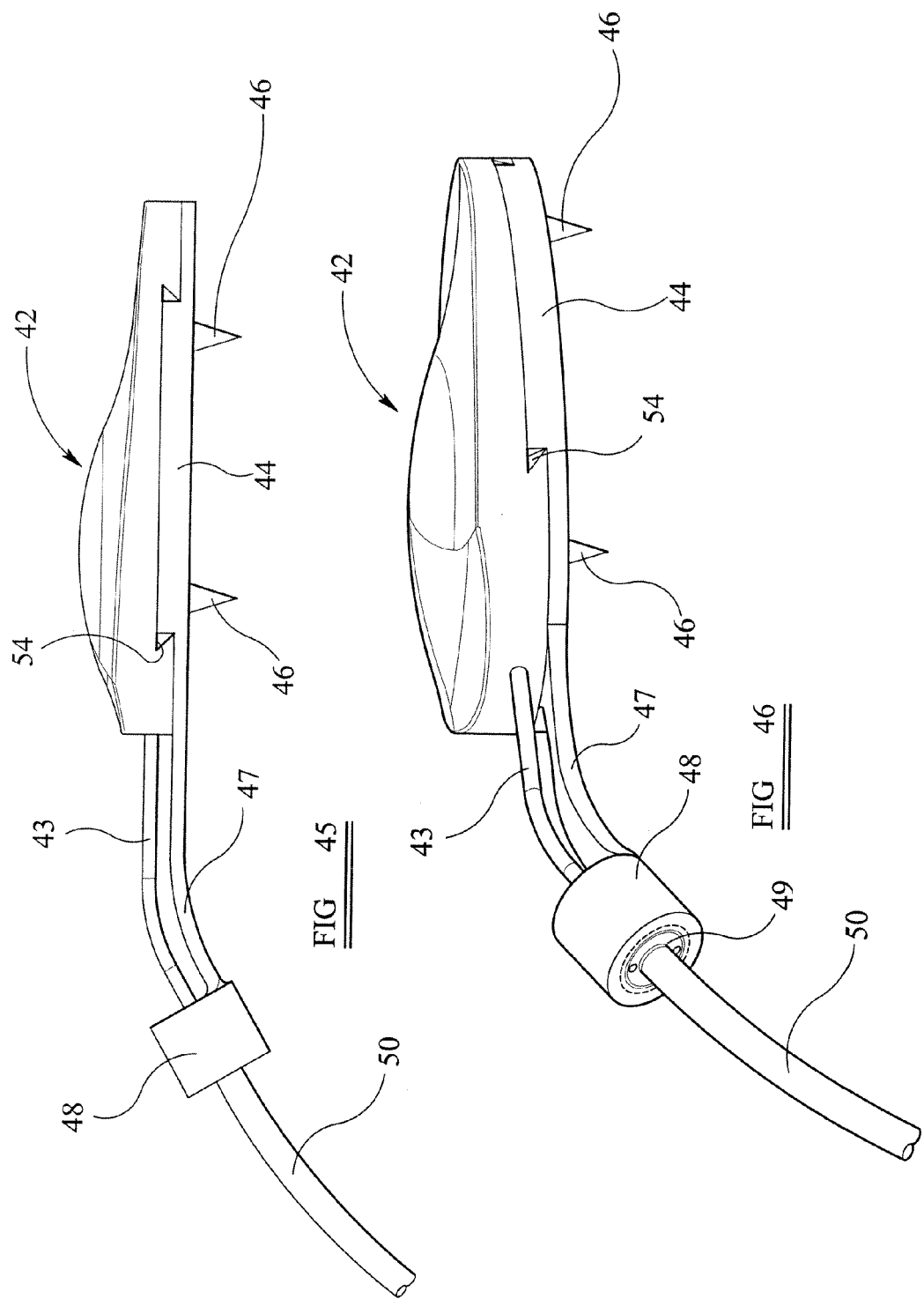

KNEE PROSTHESES

FIELD OF THE INVENTION

This invention relates to improvements in or relating to knee prostheses, and is particularly concerned with the patellofemoral interface.

BACKGROUND OF THE INVENTION

The patellofemoral joint is a troublesome area in conventional total knee replacement design. A significant number of patients are left with discomfort from the patellofemoral region following total knee replacement and others have failure such as lateral patellar mal-tracking, wear through of polyethylene patellar components, fracture of patellar components, loosening of components and fracture of the patella bone itself, requiring revision surgery.

In order to obviate the point loading and high wear using a conventional domed polyethylene patellar button, U.S. Pat. No. 4,309,778 discloses a highly conforming patellar button giving area contact. However because this type of articular surface is highly conforming to the femoral component design that it is matched to, a fixed bearing of this design would not allow the normal patellar rotation which occurs in use. The design thus had to incorporate a metallic base plate and allow rotation of the polyethylene bearing component upon that base plate.

This prior art design was however found to be susceptible to failure, and in The Journal of Arthroplasty, Volume 20, No. 2, 2005, pages 202-208, an article by Huang et al. describes failures of this type of design, pointing out that this type of patellar replacement is highly sensitive to patellar mal-tracking. As there is a finite allowable thickness of patella replacement, when a (metallic) base plate is added to a patellar button design, of necessity the polyethylene articular portion has a very thin layer, making the design highly susceptible to point loading.

An object of the invention is to provide a knee prosthesis in which the patellofemoral joint is improved. A further object is to provide an improved femoral component for use in such a knee prosthesis, and also an improved patellar articular component for use in such a knee prosthesis. A still further object is to provide a device for intra-operative checking of patellar tracking to allow correct insertion of both the femoral component and the patellar component of the knee prosthesis.

According to a first aspect of the invention there is provided a femoral component of a knee replacement comprising lateral and medial condyles, an open intercondylar area between said condyles, a patellar flange, and a patellar groove extending from said open intercondylar area to a free end of the patellar flange, characterized in that the articular surface of the patellar flange for patella contact is for a distance extending inwardly from the free end of the patellar flange configured to resist forces, in use, from a medial to a lateral direction.

Preferably a twist or roller coaster configuration is built into the femoral component to resist forces from a medial to a lateral direction. Desirably the degree of twist decreases away from said free end, and conveniently the twist is terminated at a spacing from said free end of the patellar flange lying within the open intercondylar area. In a preferred embodiment the open intercondylar area is enclosed by an intercondylar box.

According to a second aspect of the invention there is provided a patellar component of a total knee replacement comprising an articular surface formed with an off-set domed region and providing a lateral facet shaped to allow area contact, in use, and a medial facet shaped to allow line contact, in use, with an associated femoral component of said total knee replacement.

The dome is off-set medially by, for example, 5 mm, but it is preferably intended to provide a range of different off-sets available, e.g. 3 mm, 5 mm or 7 mm off-set as required. The patellar component is desirably of one piece and conveniently formed of plastics material, for example polyethylene.

In full extension, the dome has point contact with the femoral component, but in full extension the patellofemoral compressive force is lowest. In slight flexion up to 45° the dome makes line contact in the floor of the patellar groove of the femoral component. At higher degrees of flexion the dome makes no contact in the intercondylar box area and on the lateral side load is taken through the lateral facet with area contact on the lateral femoral condyle of the femoral component. On the medial side, the medial facet has a cross-section similar to a 'Mexican hat' shape, giving line contact on the medial femoral condyle.

Advantageously the patellar component has a non-articular surface with fixation means for cement fixation. In one embodiment such means could be pegs and recesses. However the component could have a modified surface for cementless fixation.

Preferably the patellar component is manufactured by oscillating a cutter blade about the centre of the lateral facet area to produce the medial facet. This method of manufacture is according to a third aspect of the invention.

According to a fourth aspect of the invention, there is provided a total knee prosthesis comprising a femoral component of said first aspect of the invention and a patellar component of said second aspect of the invention interacting therewith, in use.

According to a fifth aspect of the invention there is provided a device for intra-operative checking of patellar tracking with a total knee replacement, the device comprising a first part having a polymeric patellar component with articular surfaces matching the femoral component of the knee replacement, and an extension member for registering with a second part of the device, the second part having a portion sized to the cut surface of the patellar and with means for engagement with said cut surface, and an extension member for registering with said first part of the device, relative sliding movement being possible, in use, between said first and second parts.

A scale on one of the first or second parts of the device indicates the relative degree of sliding between the two parts. During intra-operative use, the knee is flexed throughout the whole range of movement and the amount of patellar mal-tracking measured by observation of the scale.

As, in one embodiment, the metallic base plate part of the device, the second part, makes low friction sliding contact with the patellar component of the device, then the patella with its attached soft tissues is free medio-laterally to translate to its desired position. The tracking device thus allows the Surgeon to detect any discrepancy between where the patella 'wants to be' and where the patellar component 'wants to be' and address such discrepancy.

BRIEF DESCRIPTION OF DRAWINGS

The invention will now be described, by way of example, with reference to the accompanying drawings, in which:

FIG. 4 shows transection line E-E at 90° to FIG. 3;

FIG. 5 is a view equivalent to FIG. 3, but with the section now showing the line D-D;

FIG. 6 is a view equivalent to FIG. 4 for the transection line D-D;

FIG. 10 is a view equivalent to FIG. 4 for the transection line B-B;

FIG. 11 is a view equivalent to FIG. 3 for the section along line A-A;

FIG. 12 shows the transection line A-A at 90° to FIG. 3;

FIG. 16 schematically represents a method of manufacturing a medial articular surface of the patellar component, according to a further aspect of the invention;

FIG. 17 shows the patellar component of FIG. 13 in interaction with the femoral component of FIG. 1, the position of the patellar component being as viewed from the lateral plane with the knee in full extension;

FIG. 18 shows the patellar component and femoral component at right angles to FIG. 17, the patellar component being with neutral tilt;

FIG. 22 is a view like FIG. 17, showing the position of the patellar component on the femoral component at approximately 30° flexion as viewed in the lateral plane;

FIG. 23 is a frontal projection of the patella component at the same 30° flexion as with FIG. 22;

FIG. 24 is a view corresponding to FIGS. 22 and 23 showing that the dome of the patellar component makes line contact with the floor of the patella groove of the femoral component;

FIG. 25 is a view corresponding to FIG. 17, showing the position of the patellar component on the femoral component at approximately 60° flexion as viewed in the lateral plane;

FIG. 26 is a view corresponding to FIG. 25, showing the position of the patellar component viewed in the frontal plane at 60° of flexion;

FIG. 27 shows a transverse cut though the mid-portion of the patellar component at 60° of flexion;

FIG. 37 shows a sagittal section through the lateral femoral condyle and lateral facet of the patellar component, with the patellar component in the 7° anti-clockwise rotated position;

FIG. 38 is a sagittal section through the medial femoral condyle and the medial facet with the patellar component in 60° of flexion and 7° of anti-clockwise rotation;

FIG. 39 shows one part of a device according to a further aspect of the invention for intra-operative checking of patellar tracking with a total knee replacement;

DETAILED DESCRIPTION OF PREFERRED EMBODIMENTS

Figure 1:
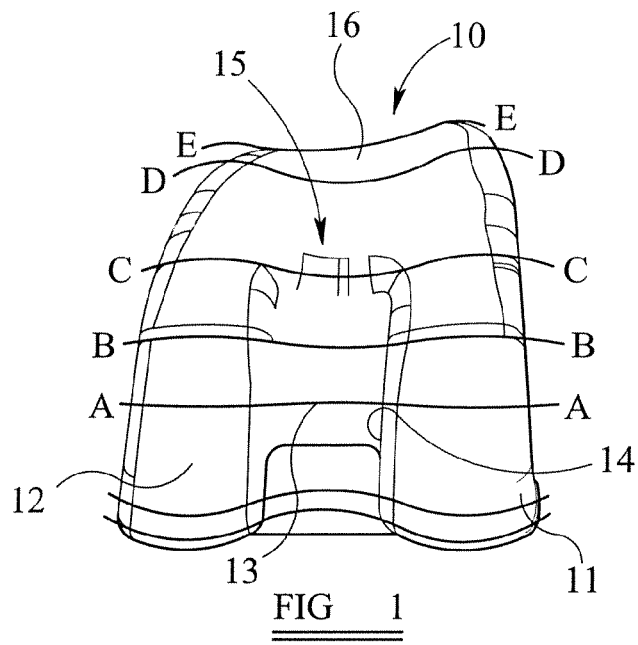
FIG. 1 is a schematic front view of a femoral component of a total knee replacement, the femoral component being according to one aspect of the present invention, the Figure showing various degrees of 'twist' incorporated into the component, the degree of twist decreasing from the line E-E, through the lines D-D, C-C, B-B, to the line A-A.

FIG. 1 shows a femoral component 10 of a knee prosthesis, the femoral component 10 comprising lateral and medial condyles 11, 12 respectively, between which is an open area 13 which, in this embodiment, is enclosed laterally and longitudinally by an intercondylar box 14. However this box could be omitted in an alternative embodiment. Extending away from the condyles 11, 12 and box 14 is a patellar flange 15, having a central patellar groove 16 extending from the box 14 to the free end of the flange 15. As shown, for example, in FIG. 3, the overall internal surface of the femoral component 10 is formed by six discrete flat surfaces 16 to 21 respectively, these, in use, matching six corresponding flat cut surfaces of the patient's femur. This particular arrangement of six flat surfaces may be formed as defined in the Applicant's co-pending UK Published Patent Application No: 2426200.

Figure 2:
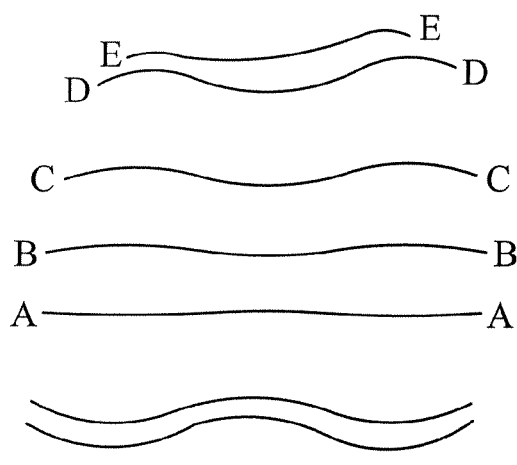
FIG. 2 very schematically shows the external profiles of the femoral component of FIG. 1 from the line E-E through to the line A-A.

According to a first aspect of the invention, as shown best in FIGS. 1 and 2, a twist is built into the femoral component, particularly the patella flange 15, in the manner of a 'roller-coaster' so that the articular surface for patella contact is gradually directed in a medial direction. This has the effect of resisting forces from a medial to a lateral direction which would cause the patella to laterally sublux or dislocate. FIG. 1 shows lines A-A through to line E-E taken in different positions through the femoral component, with the line E-E being at the free end of the patella flange, the line C-C being spaced from the line E-E substantially at the commencement of the intercondylar box 14, and the line A-A being taken part way through the length of the intercondylar box 14.

FIG. 2 shows the 'twists' of the respective lines in isolation, and from this it can be seen that the twist at line E-E is the greatest, the twist thereafter successively decreasing from line D-D through to line A-A where the twist is minimal or non-existent.

Figure 3:
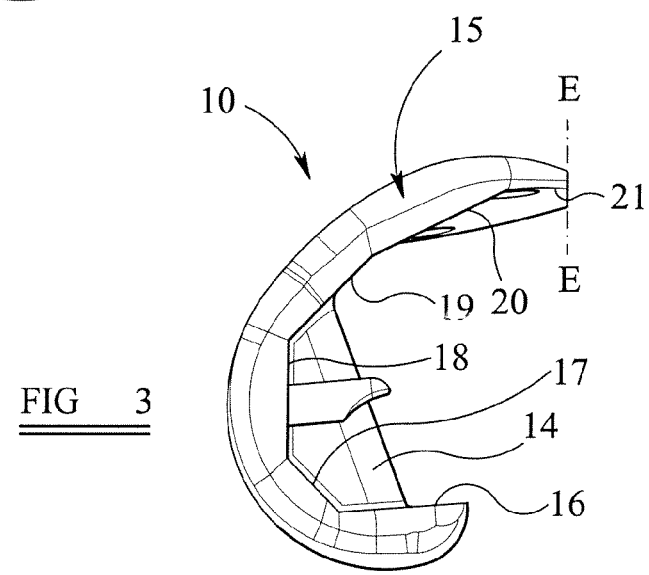
FIG. 3 shows a lateral profile of the femoral component together with the line E-E.

FIG. 3 shows a lateral profile of the femoral component 10 with a section through line E-E, whilst corresponding FIG. 4 shows transection line E-E at 90° to FIG. 3. Line P-P is a tangent to the posterior femoral condyles and line E-E is a tangent to the cut surface of the patellofemoral articulation. Line E-P is parallel to the line P-P and the acute angle between E-P and E-E therefore shows the medially directed patellofemoral articulation at this point.

FIG. 5 is a view like FIG. 3, but shows a lateral projection of the femoral component with a section along line D-D, whilst FIG. 6 is a view corresponding to FIG. 4, showing the medially directed angle at level D. It can be seen here that the acute angle between the lines D-D and D-P is substantially the same as the angle shown in FIG. 4 at the level E.

Figure 7:
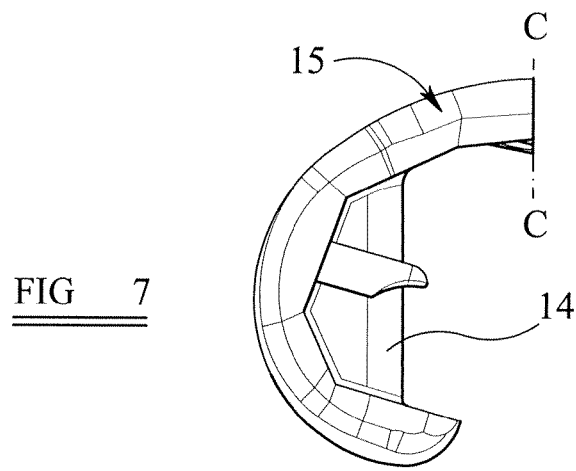
FIG. 7 is a view equivalent to FIG. 3 for the section along line C-C.
Figure 8:
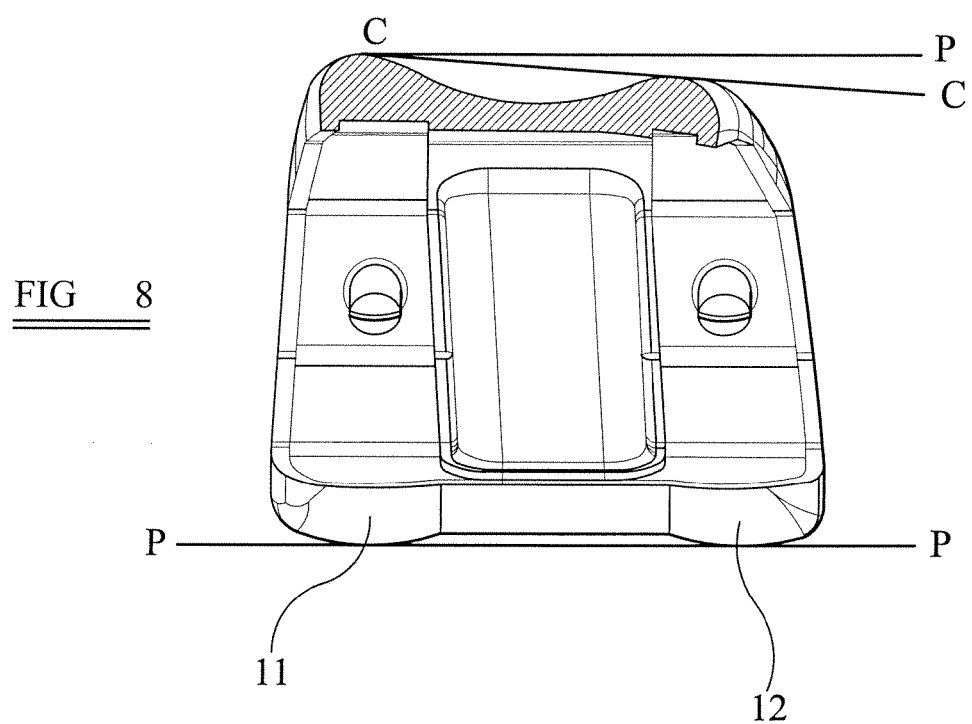
FIG. 8 is a view equivalent to FIG. 4 for the transection line C-C.

FIG. 7 is a view corresponding with FIGS. 3 and 5, showing a lateral profile of the femoral component with a section at line C-C, whilst FIG. 8, corresponding to FIG. 7, shows the medially directed patellofemoral articulation angle at point C.

Figure 9:
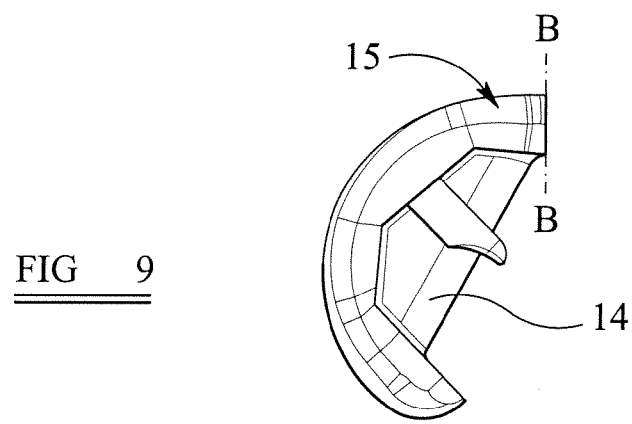
FIG. 9 is a view equivalent to FIG. 3 with the section along line B-B.

FIG. 9, corresponding to FIGS. 3, 5 and 7, shows the lateral projection of the femoral component with a section along line B-B, whilst FIG. 10, corresponding to FIGS. 4, 6 and 8, shows an ever decreasing medially directed angle between lines B-B and B-P at the level B.

Finally FIG. 11 corresponding to FIGS. 3, 5, 7 and 9, shows the lateral projection of the femoral component with section at level A-A, with corresponding FIG. 12 showing, for a view corresponding to FIGS. 4, 6, 8 and 10, that the 'roller-coaster' is fully unwound so that there is now no angle between the line A-A and the posterior femoral condyles.

Figure 13:
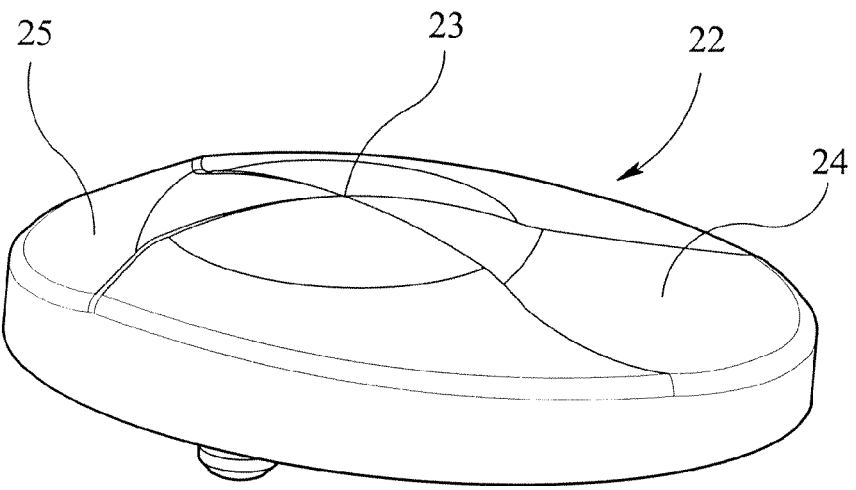
FIG. 13 is a perspective view of a patellar component of another aspect of the invention, showing an articular surface thereof.
Figure 14:
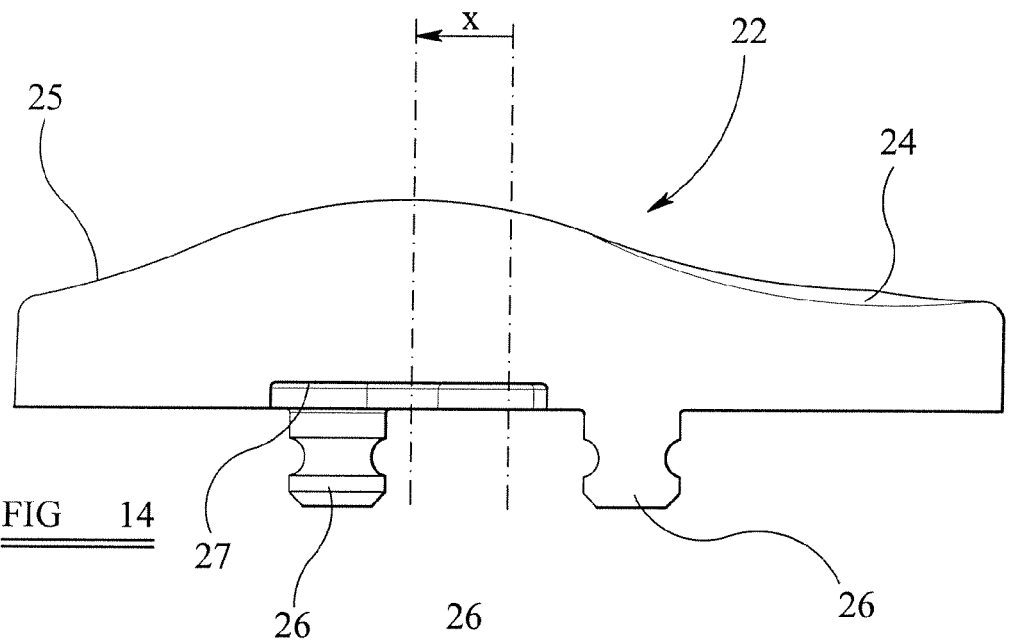
FIG. 14 is a horizontal cross section through the mid-patellar component with a degree of off-set of a dome of the component being shown.
Figure 15:
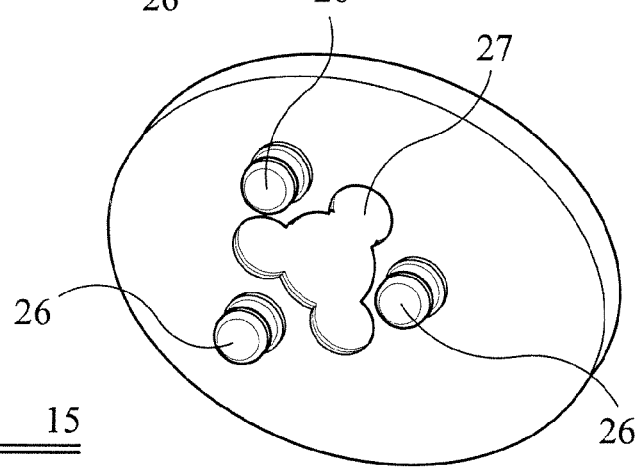
FIG. 15 is a perspective view of the underside surface of the patellar component.

FIGS. 13 to 15 show a patellar component 22 in the form of a one-piece plastics material button, for example of polyethylene, the button having, as viewed, an upper surface, which is internal, in use, and a lower surface which is external, in use, and is for fixation to the remnant human patella, using an acrylic grouting agent or cement or other suitable fixing means. The internal (upper) articular surface of the button is in the form of an off-set dome 23 with a lateral facet 24 shaped to allow area contact, and a medial facet 25 shaped to allow line contact. In full extension, the dome of this patellar button has point contact, but in full extension the patellofemoral compressive force is lowest. In slight flexion up to 45° the dome 23 makes line contact in the floor of the patella groove 16 of the femoral component. At higher degrees of flexion the dome 23 makes no contact in the area of the intercondylar box 14 and on the lateral side load is taken through the lateral facet 24 with area contact on the lateral femoral condyle of the femoral component 10 and on the medial side the medial facet 25 has a cross-section similar to a 'Mexican hat' shape, giving line contact on the medial femoral condyle 12.

FIG. 14 shows a horizontal cross-section through the mid-patellar button. As can be seen from this Figure, the dome is off-set in the medial direction by a distance 'x'. In the embodiment shown there is 5 mm of medial off-set of the dome. However it is intended, as will be referred to hereinafter, to have a range of different off-sets available, for example 3 mm off-set, 5 mm off-set or 7 mm off-set.

FIG. 15 is a view of the non-articular surface of the patella button, and in the example shown this surface is provided with three pegs 26 and an associated recess 27 for cement fixation to the remnant human patella. However this design could also have a modified non-articular surface for cementless fixation also.

FIG. 16 shows how the medial facet 25 is manufactured. A cutter blade F-F is oscillated about the centre of the area of the lateral facet 24 to produce the medial facet 25. This ensures that when the patella rotates in use, then the new patella articular surface rotates about the centre of the lateral facet area, retaining lateral area contact and on the medial side line contact is maintained on the medial facet 25.

FIGS. 17 to 38 show the interaction of the patellar component 22 with the femoral component 10 of FIGS. 1 to 12. FIG. 17 shows the position of the patellar button 22 on the femoral component as viewed from the lateral plane with the knee in full extension, whilst FIG. 18 shows that in full extension, the femoral component 10 does not constrain the patellar button 22 or the patella into any particular direction of tilt. Shown in FIG. 18 is the patella with neutral tilt.

Figure 19:
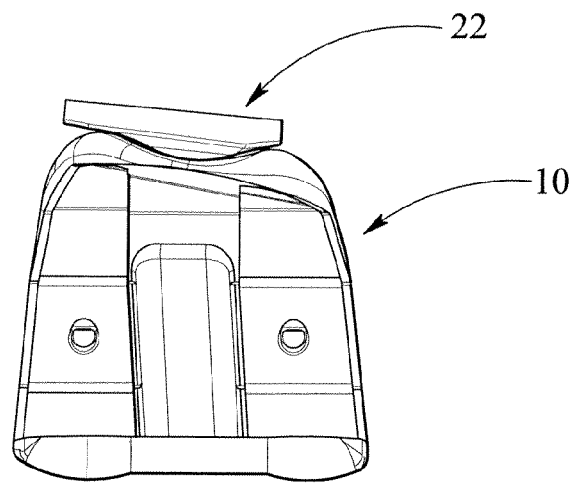
FIG. 19 is a view corresponding to FIG. 18, with the patellar component with a medially directed tilt.
Figure 20:
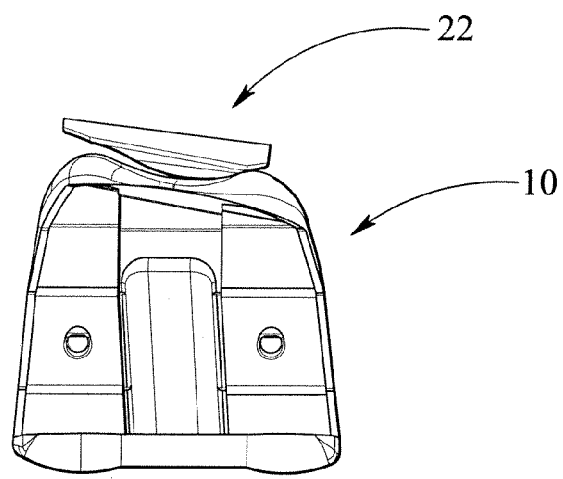
FIG. 20 is a view like FIG. 19, showing the patellar component entering the patellar groove from a medial direction.
Figure 21:
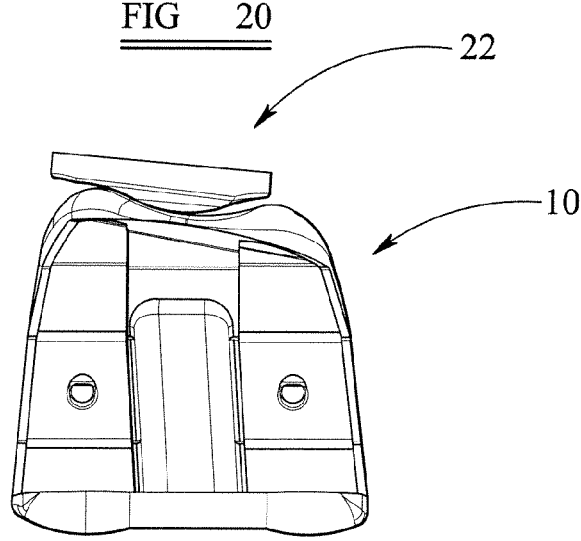
FIG. 21 is a view like FIG. 19, showing the patellar component entering the patellar groove from a lateral direction.

FIG. 19 shows the patella and the patellar button with a medially directed tilt. In other words, neither the medial nor the lateral facet of the patella button make contact in normal use with the femoral component in full extension, and the soft tissues are therefore able to apply whatever tilt they desire on the patella and the patellar button. The contact between the dome 23 of the patella button and the patellar groove 16 in full extension is point contact. This is not regarded as a concern because in this position of full extension the patellofemoral compressive forces are at their lowest. It can be seen that in extension the radius of curvature at the base of the patella groove on the femur is greater than the radius of curvature of the dome 23 of the patella button. This means that the patella track on the femur in common with previous total knee replacement designs has a 'funnel' shape at its most proximal end, thus 'catching' the patella button from whatever direction it enters the patellar groove. FIG. 20 shows the patellar button entering the 'funnel' of the patellar groove 16 from a medial direction, whilst FIG. 21 shows the patellar button arriving from a lateral direction with the patella groove 'funnel' at its most proximal end, 'catching' the patella button.

FIG. 22 shows the position of the patellar button 22 on the femoral component 10 at approximately 30° of flexion as viewed in the lateral plane. FIG. 23 showing a frontal projection of the patellar button 22 at the same 30° of flexion.

FIG. 24 shows that the 'funnel' effect of the top of the patellar groove has now disappeared, and the dome of the patella makes its line contact with the floor of the patellar groove of the femoral component. The medial and lateral facets of patella start to engage the respective parts of the femur, and a medially directed tilt of the patellar button and patella is created.

FIG. 25 shows the position of the patella on the femur at approximately 60° of flexion as viewed in the lateral plane, whilst FIG. 26 shows the position of the patellar button viewed in the frontal plane at 60° of flexion. FIG. 27 shows a transverse cut through the mid-portion of the patellar button in 60° of flexion, and it can be seen that the dome 23 of the patellar button no longer makes contact with the femur as it is now in the box region around the patellar groove 16. It can be seen from this transverse view that there is line contact of the lateral facet on the lateral femoral condyle and line contact of the medial facet on the medial femoral condyle.

Figure 28:
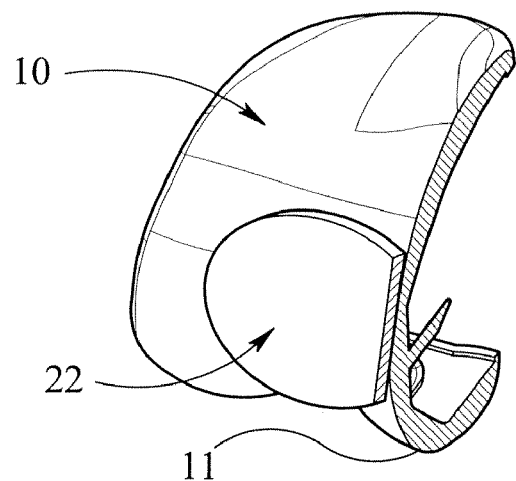
FIG. 28 shows a sagittal section through the lateral femoral condyle and the lateral facet of the patellar component at 60° of flexion.
Figure 29:
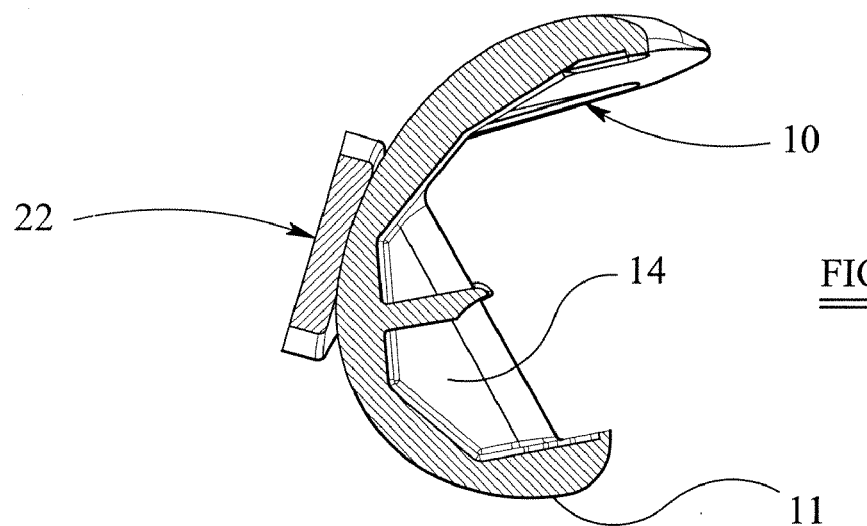
FIG. 29 is a view normal to the sagittal section of FIG. 28 showing line contact between the lateral facet of the patellar component and the lateral femoral condyle as viewed in this plane.
Figure 30:
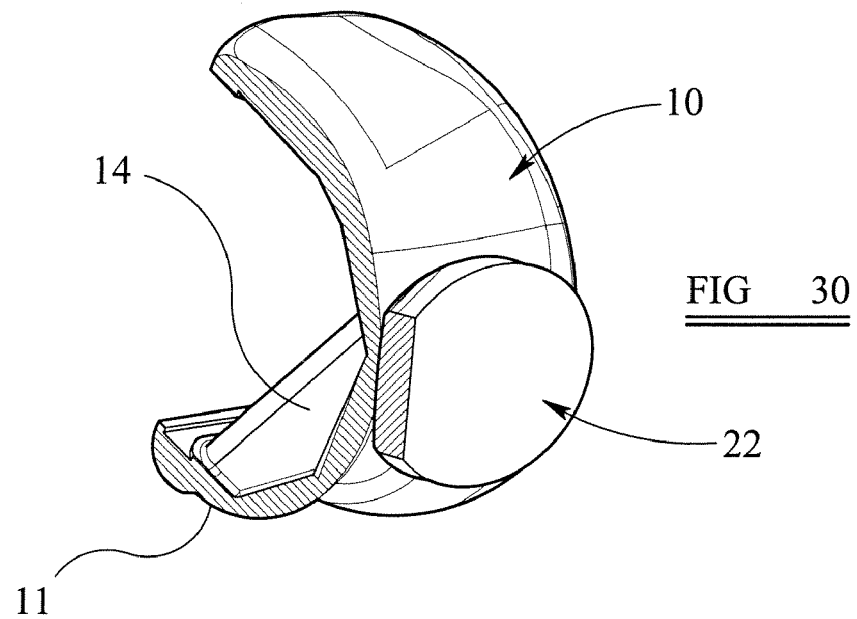
FIG. 30 shows a sagittal section through the medial femoral condyle and the medial facet of the patellar component at 60° of flexion.
Figure 31:
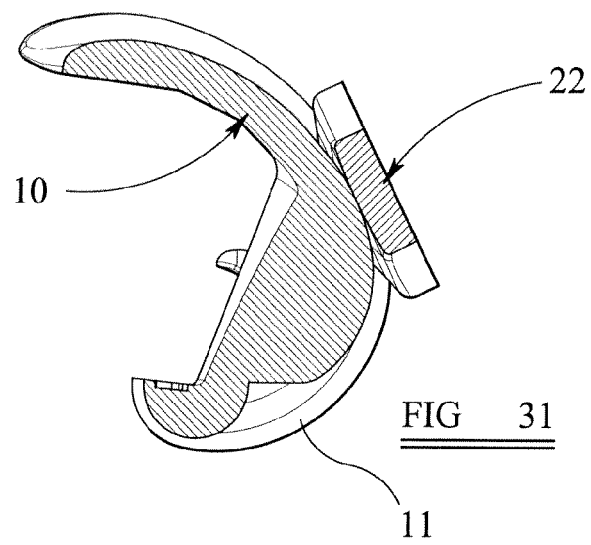
FIG. 31 is a view normal to a sagittal plane of FIG. 30 showing that in this projection, point contact only occurs between the medial facet of the patellar component and the medial femoral condyle.

FIG. 28 shows a sagittal section through the lateral femoral condyle and the lateral facet of the patella, whilst FIG. 29 is a view normal to the section of FIG. 28, showing line contact between the lateral facet of the patella and the lateral femoral condyle as viewed in this plane. It will be appreciated that since there is line contact visible between the lateral facet and the lateral femoral condyle, both in the transverse and sagittal planes, this means that area contact exists between the lateral facet of the patella and the lateral femoral condyle. FIG. 30 is a similar view to FIG. 28, but shows a sagittal section through the medial femoral condyle and the medial facet of the patella at 60° of flexion, whilst FIG. 31 is a view normal to the sagittal plane view of FIG. 30. This shows that in this projection point contact only occurs between the medial facet of the patella and the medial femoral condyle. However with line contact showing on the transverse plane and point contact showing on the sagittal plane, this means that line contact occurs between the medial facet of the patella and the medial femoral condyle.

Figure 32:
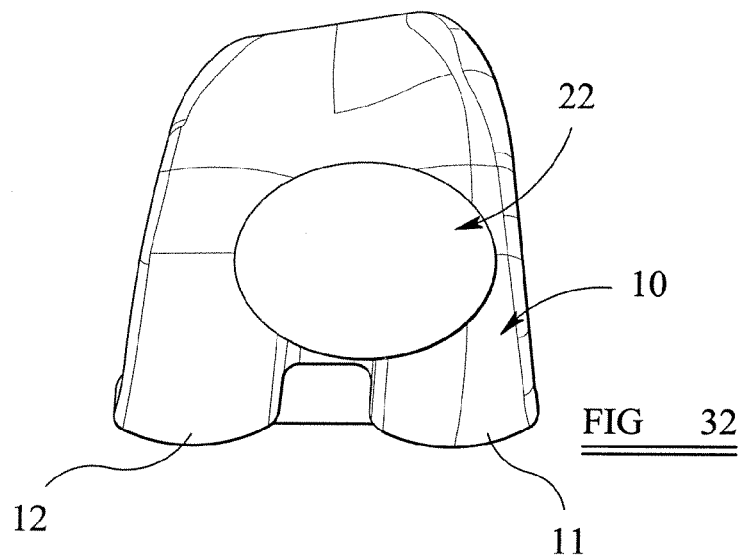
FIG. 32 shows the patellar component on the femoral component with neutral rotation.
Figure 33:
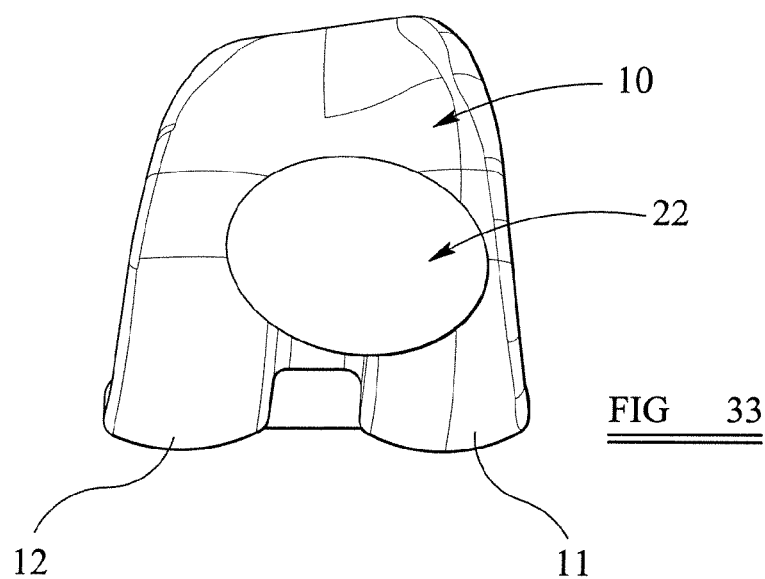
FIG. 33 is a view similar to FIG. 32, showing the patellar component on the femoral component with 7° of clockwise rotation.
Figure 34:
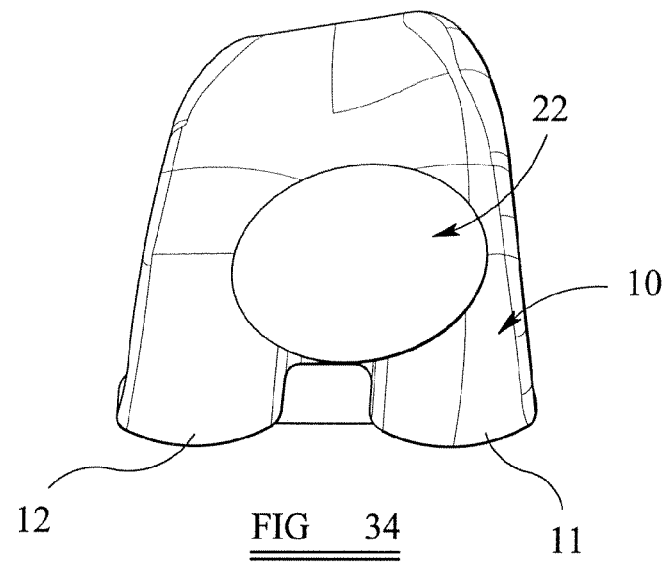
FIG. 34 is a view corresponding to FIG. 32, but showing the patella component on the femoral component with 7° of anti-clockwise rotation.
Figure 35:
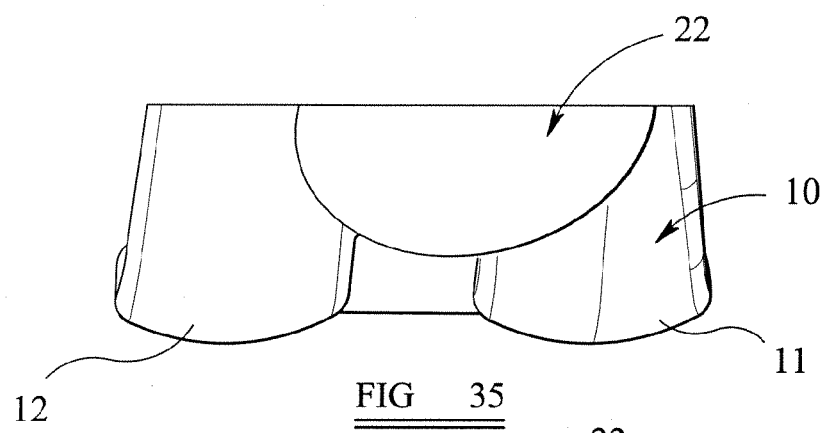
FIG. 35 is a view like FIG. 32, showing a transverse section through the mid-patellar component with 7° of anti-clockwise rotation.

FIG. 32 shows the patellar button on the femoral component with neutral rotation, whilst FIG. 33 shows the patella button on the femur with 7° of clockwise rotation, with FIG. 34 showing the patella on the femur with 7° of anti-clockwise rotation. FIG. 35 shows a transverse section through the mid-patella with 7° of anti-clockwise rotation.

Figure 36:
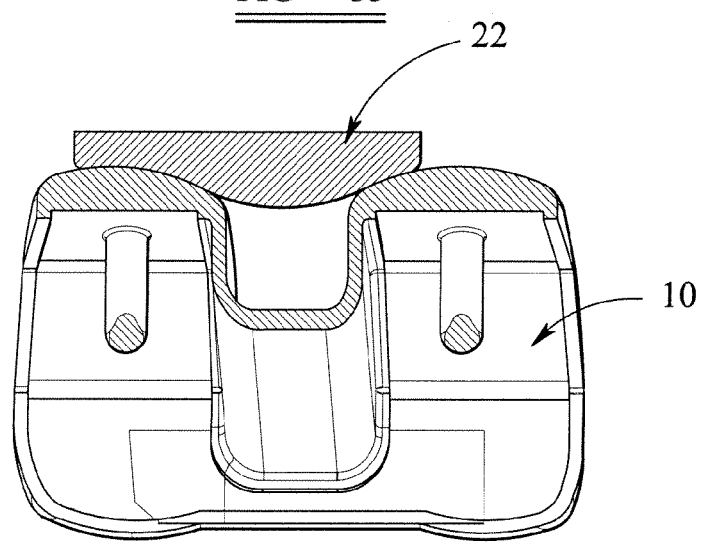
FIG. 36 shows in the transverse plane of FIG. 35, line contact of the medial facet on the medial femoral condyle and lateral facet on the lateral femoral condyle is maintained with the patellar component.

FIG. 36 shows that in the transverse plane illustrated, line contact of the medial facet on the medial femoral condyle and lateral facet on the lateral femoral condyle is maintained, the transverse plane being that referred to in FIG. 35.

FIG. 37 shows a sagittal section through the lateral femoral condyle and lateral facet of patella with the patella in a 7° anti-clockwise rotated position. This still shows area contact between the lateral facet of the patella and the lateral femoral condyle. The fact that there is again line contact showing on both the sagittal cut and the transverse cut means that lateral area contact has been maintained despite 7° of rotation. FIG. 38 is a sagittal section through the medial femoral condyle and the medial facet with the patella in 60° of flexion and 7° of anti-clockwise rotation. This shows point contact when viewed in the sagittal plane. However, since in the 7° rotated position there is still line contact on the transverse view and point contact on the sagittal view means that despite 7° of rotation of the patellar button on the femur, medial line contact is maintained.

According to another aspect of the invention, there is provided a patellofemoral alignment guide which is an instrument intended for intra-operative checking of patellar tracking to allow correct insertion of both the femoral component and the patellar button of a total knee replacement.

Figure 40:
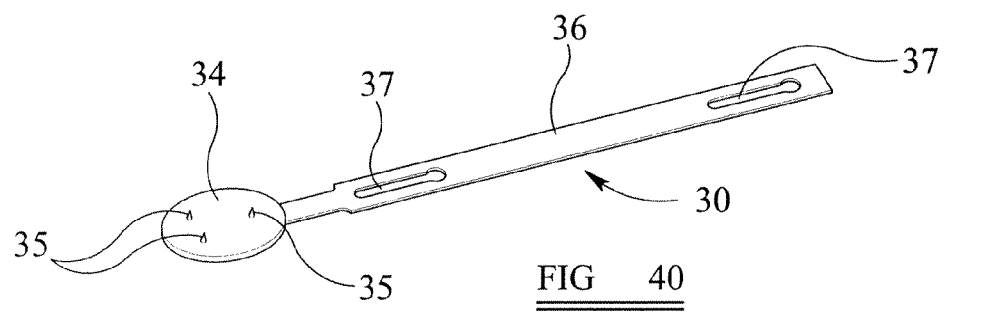
FIG. 40 shows a further part of the device for intra-operative checking of patellar tracking.
Figure 41:
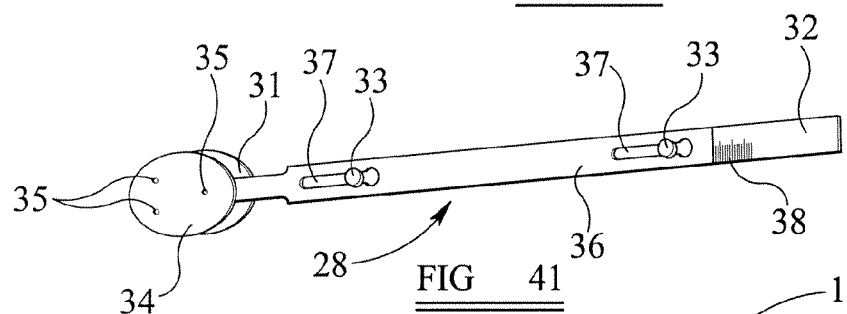
FIG. 41 shows the two parts of the device shown in FIG. 39 and FIG. 40 fitted together.
Figure 42:
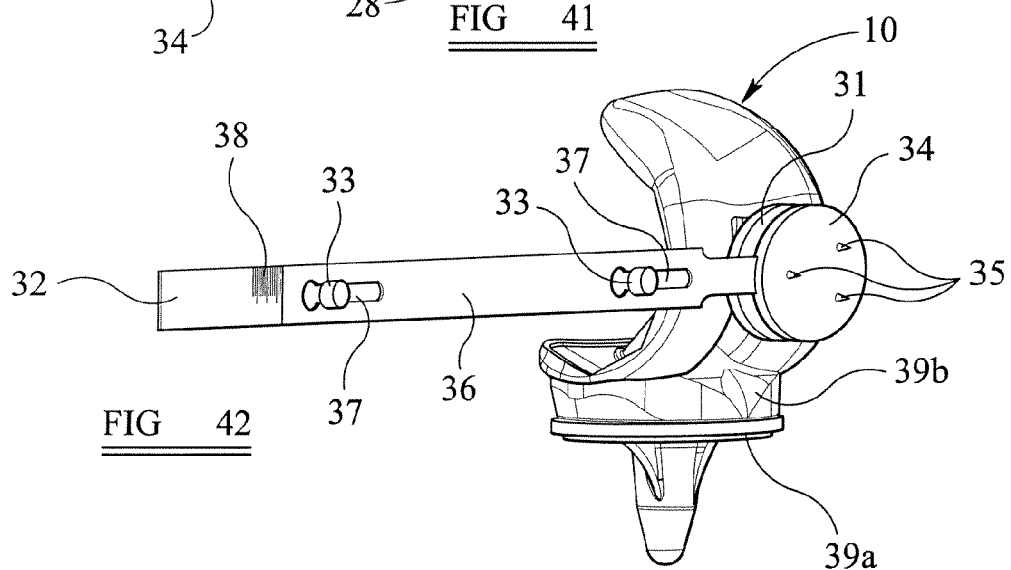
FIG. 42 shows schematically the patellofemoral alignment guide of FIG. 41 in use with the knee flexed to approximately 55°.
Figure 43:
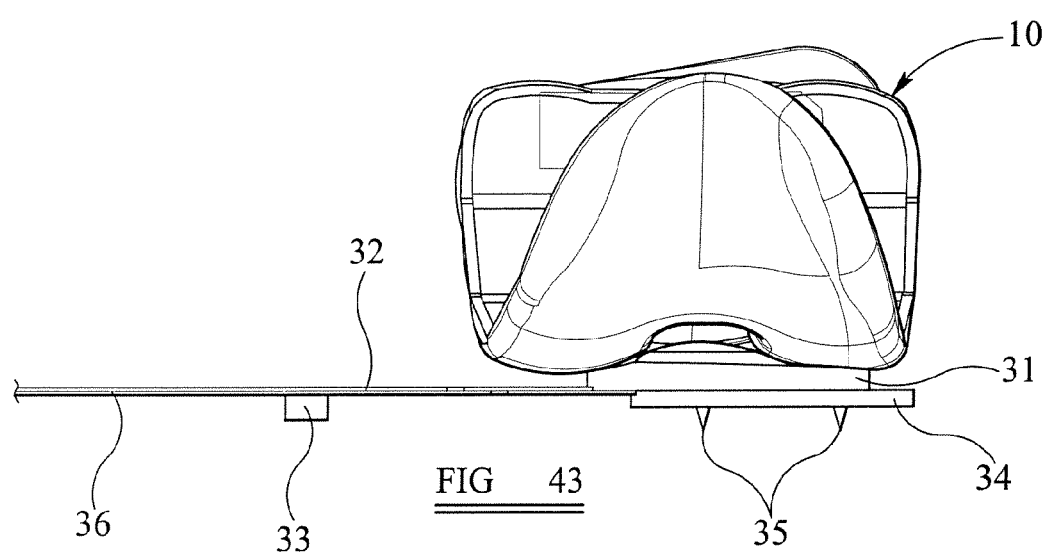
FIG. 43 shows a further view of the alignment guide in use at 90° to FIG. 42.

The structure of this instrument 28 is shown in FIGS. 39 to 41, while FIGS. 42 and 43 show the instrument in use in conjunction with the replacement knee components.

The instrument consists of two parts, a first part 29 being shown in FIG. 39, a second part 30 being shown in FIG. 40 and the instrument with the two parts 29 and 30 assembled together being shown in FIG. 41. From FIG. 39 it can be seen that the first part of the instrument has a polymeric patellar button trial component 31 with articular surfaces designed to match the femoral component being inserted into the patient. As illustrated the articular surfaces are in the form of the embodiment hereinbefore described, but this instrument could be applied to any total knee replacement design with a polymeric patellar button surface made to match the particular femoral component being inserted. Extending from the medial side of the patellar button trial component 31 is an extension member in the form of a flat flexible metallic rod 32 which on its underside is provided with two or more lugs 33 for registering, i.e. for sliding and locking engagement with the second part 30 of the instrument. The second part of the instrument, as shown in FIG. 40, consists of a metallic base plate 34 sized to the cut surface of the patella. Desirably this base plate should be of the same size as the patellar button that is being inserted. Base plate 34 has short metallic spikes 35 for temporary engagement into the cut surface of the patella. Extending from the medial side of the base plate is a flat metallic rod 36 similar to the rod 32 of the first part of the instrument. The rod 36 is provided with a pair of spaced elongated keyhole-like openings 37 to allow the second part to register with the first part by means of the lugs 33 extending through said openings which allow locking and sliding engagement between the two parts, as shown in one position in FIG. 41. That Figure shows the two parts of the instrument fitted together, and when sliding of one part of the instrument occurs on another, then the amount of such sliding can be read-off on a millimeter or other scale, which in the example shown, is marked on rod 32, being denoted by the numeral 38. It will be understood that in alternative embodiment, the scale could be provided on the second part 30, and it will also be understood that the respective designs of the extension members can be varied as required.

FIG. 42 is a schematic view of the patellofemoral alignment guide instrument, in use, with the knee flexed to approximately 55°, in this example. Not only is there shown the replacement femoral component 10, but there is also shown the tibial base plate 39a and a plastics material bearing component 39b of the total knee replacement or prosthesis. It is intended that during intra-operative use, the knee is flexed throughout the full range of movement, and the amount of patellar mal-tracking measured by observation of the scale of the instrument.

FIG. 43 shows that because the patellar button, i.e. the trial component 31, of this instrument is highly congruent with the respective femoral component, then during flexion and extension of the knee, this patellar button part of the instrument will stay normally aligned with the femoral component. Since the metallic base plate part 34 of the instrument makes low friction sliding contact with the patellar button part of the instrument, then the patella with its attached soft tissues is free to medio-laterally translate to its desired position.

A further, more preferred form of patellofemoral alignment guide instrument is shown in FIGS. 44 to 49. As with the first embodiment of such an instrument, shown in FIGS. 39 to 43, the instrument of FIGS. 44 to 49 also consists of two parts, namely a first part 40 and a second part 41 of plastics material.

The first part 40 of the instrument has a polymeric patellar button trial component 42 with articular surfaces designed to match the femoral component being inserted into the patient. As with the instrument of the first embodiment, the patellar button surface could be made to match the particular femoral component being inserted.

Extending from the medial side of the patellar button trial component is a flexible wire 43, this wire forming an extension member for registering with the second part 41 of the instrument, as will be described.

The second part 41 consists of a base plate 44 sized to the cut surface of the patella. Desirably this base plate should be of the same size as the patellar button that is being inserted.

The base plate 44 has three circular opening 45 therein and three spikes 46 for temporary engagement into the cut surface of the patella.

Figure 44:
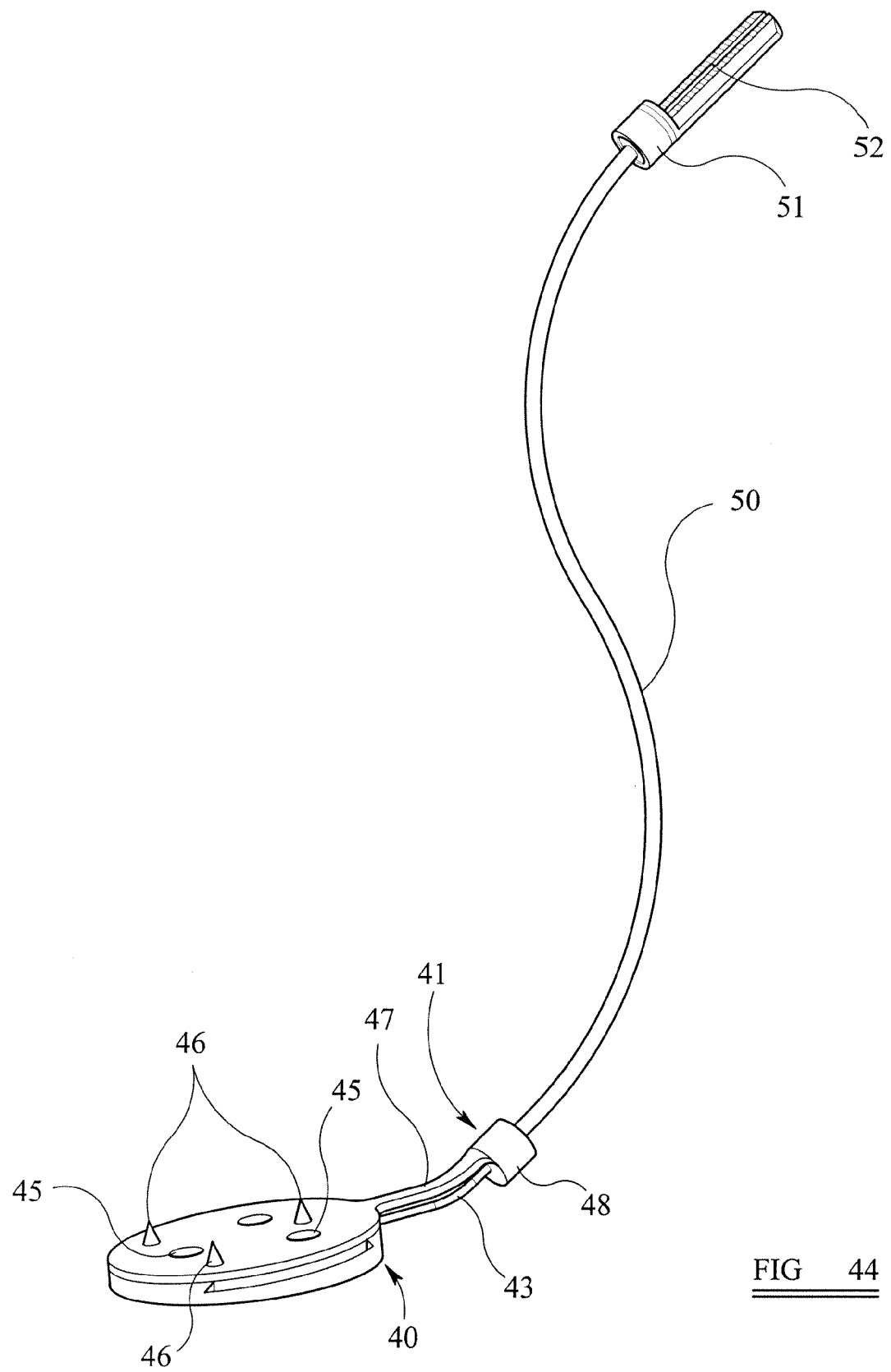
FIG. 44 shows an alternative form of patellofemoral alignment guide to that shown in FIG. 41, FIGS. 45 and 46 are respective fragmentary enlarged side and perspective views of the guide of FIG. 44.

Extending from the medial side of the base plate 44 is an extension member in the form of an integral flexible strap part 47 which at its end is formal as an integral, short cylindrical hollow sleeve 48. As shown best in FIG. 46, there is fixed within the sleeve 48, and filling it, a tubular insert 49 through which centrally extends one end of a hollow elongated flexible tube 50 of considerable length, as shown in FIG. 44.

The tube 50 is fixed to the insert 49, and at its other end it is fixed to and extends into one end of a short cylindrical sleeve 51. Extending from the other end of the sleeve is an integral reference portion, having a scale 52 on a flat surface through which centrally extends a part-circular cross-section, open-topped channel 53. The tube thus also forms part of the extension member for registering with the first part 40.

Figure 47:
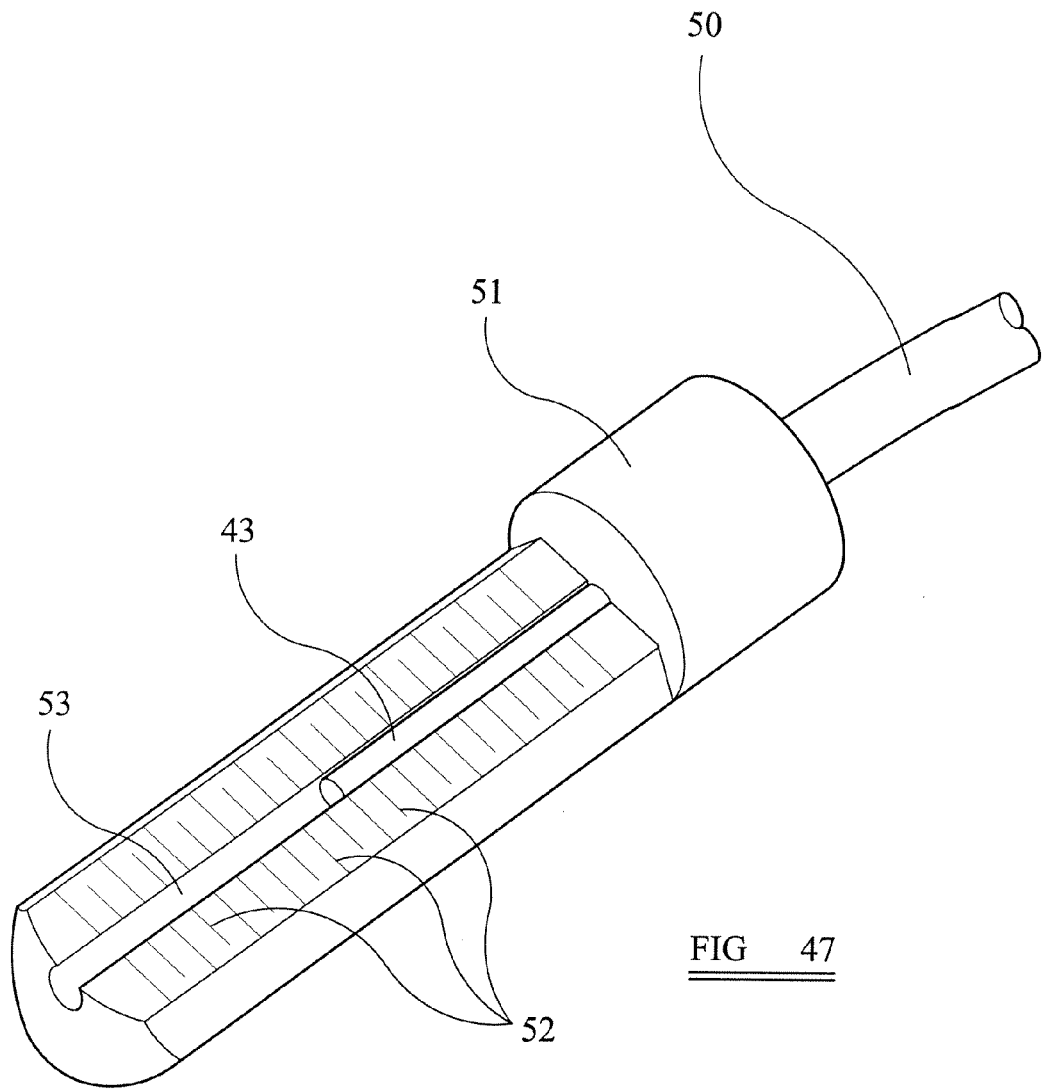
FIG. 47 is a fragmentary enlarged perspective view of an end of the guide of FIG. 44 at which measurements are taken.
Figure 48:
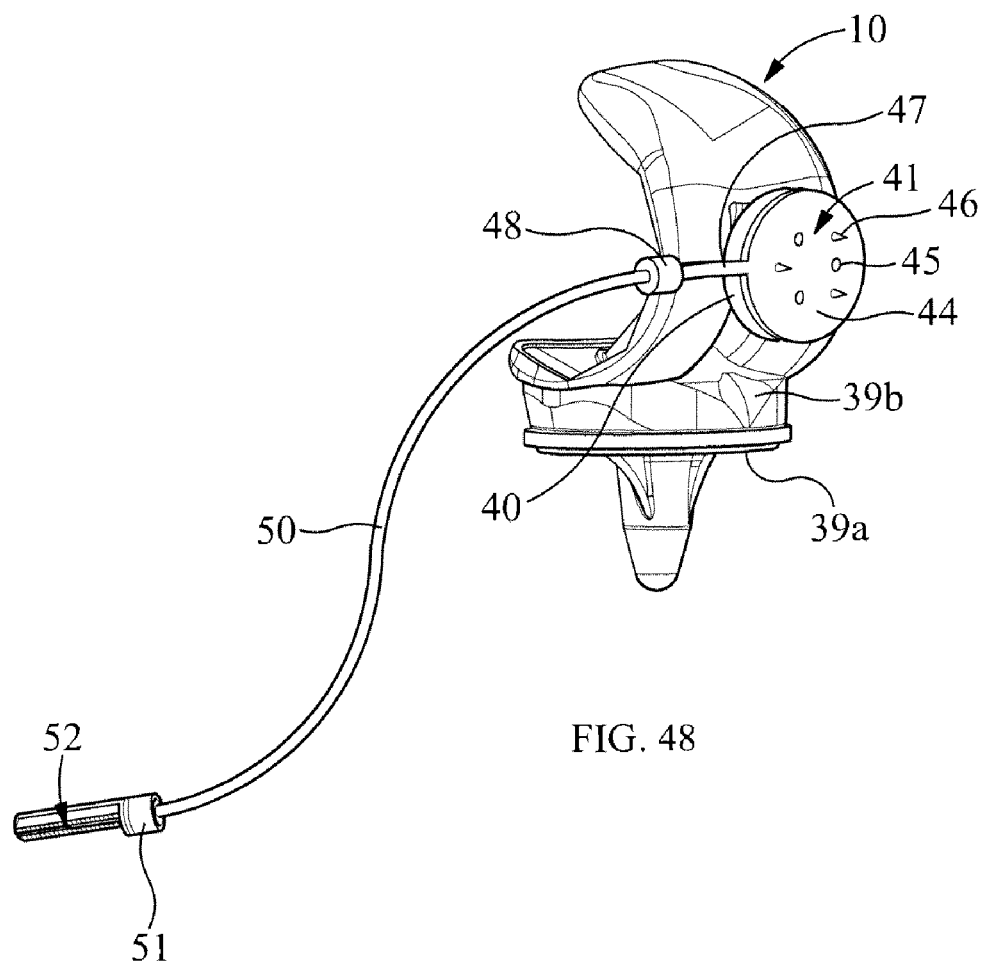
FIGS. 48 and 49 are respective side and topdown views of the guide of FIG. 44 used with the femoral component of FIG. 43.
Figure 49:
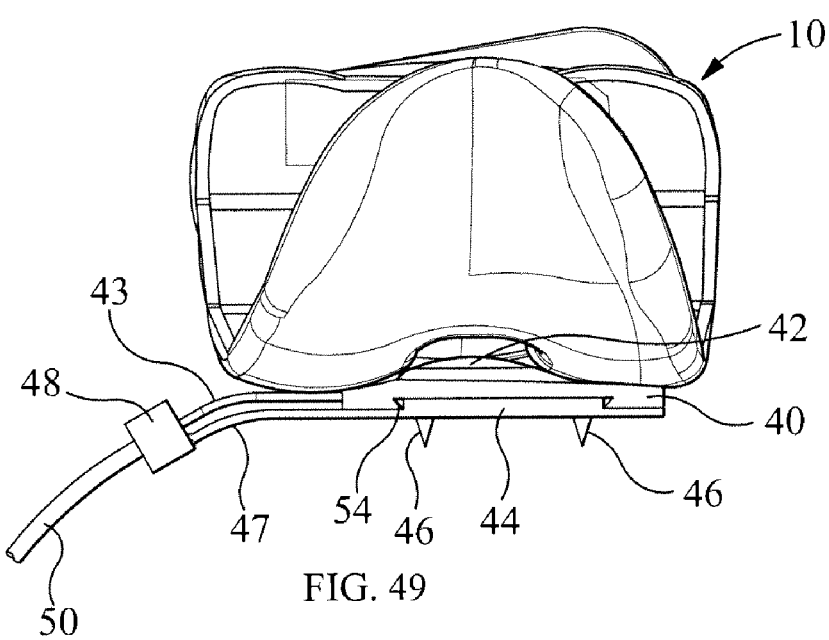

When the parts 40 and 41 are fitted together, as shown in FIGS. 44 to 47, a configured part of the base plate of the second part 41 is received in a recess 54 in the undersurface of the patellar button trial component 42, which recess has undercut (dovetail) sides. The flexible wire 43 extends from the component by following the path of the strap 47 and then being received through the tube 50, relative to which it can slide. The free end of the wire passes out of the tube 50 through its sleeve 51 to emerge disposed within the channel 53, as shown in FIG. 47.

With the arrangement described and illustrated, it will understood that the instrument of FIGS. 44 to 49 is used with a flexed knee in effectively the same manner as for the first embodiment of the instrument shown in FIGS. 42 and 43. The main difference is of course in relation to the way in which the amount of any patellar mal-tracking is measured. Accordingly relative sliding movement between the parts 40 and 41 is translated into sliding movement of the wire in the channel 53, the position of the free end of the wire being measured against the scale 52. The use of this type of flexible Bowden cable has been found to be better than the arrangement of FIGS. 39 to 43.

SUMMARY

The tracking instrument therefore allows the Surgeon to detect any discrepancy between where the patella 'wants to be' and where the patellar button 'wants to be'. During the operation, the Surgeon can address any discrepancy by several maneuvers. If, for example, the patella is laterally mal-tracking, then the Surgeon could address this by:

1) Laterally displacing the trial femoral component on the femur, thus lateralizing the patellar groove.

2) Medially displacing the tracker base plate on the cut surface of the patella, provided enough bone exists to allow such medial displacement.

3) Choosing a patellar button with a greater off-set, e.g. choosing a 5 mm off-set or a 7 mm off-set patellar button in preference to a 3 mm patellar off-set button.

4) In fixed bearing knee designs, but not appropriate in this illustrated case, the Surgeon could alter the rotational alignment of the trial tibial component upon the tibia, provided enough bone exists to allow such rotational re-alignment.

5) A lateral retinacular release could be performed, but this would be regarded as a last resort measure, as lateral retinacular release carries morbidity because of bruising and also risks injuring the blood supply to the patella.

What is claimed is:

1. A device for intra-operative checking of patellar tracking with a total knee replacement, the device comprising a first part having a polymeric patellar component with articular surfaces matching a femoral component of the knee replacement, and an extension member for registering with a second part of the device, the second part having a portion sized to a cut surface of a patellar and with means for engagement with the cut surface, and an extension member for registering with said first part of the device, relative sliding movement being possible, in use, between said first and second parts and wherein the extension members of the first and second parts are flexible and the extension member of the first part is in a form of a flexible wire which extends through a flexible tube of said second part.

2. A device as claimed in claim 1, wherein a scale on one of the first or second parts of the device indicates a relative degree of sliding between the first part and the second part.

3. A device as claimed in claim 2, wherein the scale is configured to indicate an amount of patellar mal-tracking when a knee is flexed through a whole range of movement while the patellar component of the first part is applied to the femoral component of the knee replacement residing within the knee.

4. A device as claimed in claim 2, wherein, a free end of the flexible wire registers with said scale on the second part to indicate the relative degree of sliding between the first part and the second part.

5. A device as claimed in claim 4, wherein said scale is formed on a reference portion at an end of the flexible tube remote from said portion of the second part sized to the cut surface of the patella.

6. A device as claimed in claim 5, wherein the reference portion defines a flat surface carrying said scale and having an open-topped channel therein, in which said free end of the flexible wire is slidably received.

7. A device as claimed in claim 4, wherein there is a flexible strap part between said portion of the second part sized to the cut surface of the patella and said flexible tube.

8. A device as claimed in claim 7, wherein the tube extends from a sleeve at one end of the strap.

9. A device as claimed in claim 1, wherein the means of the second part for engagement with the cut surface are a plurality of spikes extending from an opposite surface of the second part to that which effects relative sliding movement with the first part.

10. A device as claimed in claim 1, wherein the patellar component of the first part has a recess in which is received part of the portion of the second part sized to the cut surface of the patellar.

11. A device as claimed in claim 10, in which said recess has undercut sides.

12. A device as claimed in any claim 1, wherein the second part is of plastics material.

13. A device claimed in claim 1, wherein the second part is a metallic base plate part of the device.

14. A device as claimed in claim 4, wherein the device is configured such that when the second part is in low friction sliding contact with the patellar component of the device, the patella with the patella's attached soft tissues is free medio-laterally to translate to the patella's desired position.

* * * * *